United States Patent [19]

Cohen et al.

[11] Patent Number: 5,236,362
[45] Date of Patent: Aug. 17, 1993

[54] ROOT CANAL FILLING MATERIAL AND ADHESIVE COMPOSITION

[75] Inventors: Brett I. Cohen, Nanuet; Barry L. Musikant, New York, both of N.Y.

[73] Assignee: Essential Dental Systems, Inc., South Hackensack, N.J.

[21] Appl. No.: 920,157

[22] Filed: Jul. 27, 1992

Related U.S. Application Data

[62] Division of Ser. No. 775,289, Oct. 11, 1991, abandoned.

[51] Int. Cl.⁵ .......................... A61C 5/00; A61K 6/08
[52] U.S. Cl. .................................. 433/228.1; 433/81; 433/224; 433/226; 523/116
[58] Field of Search ..................... 433/224, 228.1, 226, 433/81; 523/116

[56] References Cited

U.S. PATENT DOCUMENTS

| | | | |
|---|---|---|---|
| 3,925,895 | 12/1975 | Kliment et al. | 433/224 |
| 4,425,094 | 1/1984 | Tateosian et al. | 433/228 |
| 4,505,973 | 3/1985 | Neet et al. | 252/511 |
| 4,525,147 | 6/1985 | Pitz et al. | 433/224 |
| 4,621,106 | 11/1986 | Fracalossi et al. | 252/511 |
| 4,692,272 | 9/1987 | Goswami et al. | 523/458 |
| 4,921,623 | 5/1990 | Yamaguchi et al. | 523/458 |
| 4,931,479 | 6/1990 | Morgan | 252/514 |
| 5,043,102 | 8/1991 | Chen et al. | 523/459 |
| 5,071,593 | 12/1991 | Takahashi et al. | 252/511 |

FOREIGN PATENT DOCUMENTS

| | | | |
|---|---|---|---|
| 0001993 | 1/1967 | Japan | 523/458 |
| 0051771 | 3/1985 | Japan | 523/459 |

OTHER PUBLICATIONS

Chapter 5 "Root Canal Filling: Procedures and Materials", Endontics—Science and Practice, André Schroeder, 1981 pp. 165–196.

Primary Examiner—Paul R. Michl
Assistant Examiner—LaVonda DeWitt
Attorney, Agent, or Firm—Gottlieb, Rackman & Reisman

[57] ABSTRACT

A composition for endodontically treating a root canal is provided. The composition uses a thermoset resin based material adapted for insertion into the root canal of a dental patient and an adhesive material suitable for maintaining the polymer based material in the root canal. Either one or both of the thermoset resin based material and the adhesive material is conductive. As a result, the dental practitioner is able to determine where the apex of the root canal is located by means of measuring the conductance between the thermoset resin based material and the oral mucosa and periodontal ligament. This facilitates the filling of the root canal with the polymer based material.

66 Claims, No Drawings

ROOT CANAL FILLING MATERIAL AND ADHESIVE COMPOSITION

This application is a division of application Ser. No. 07/775,289, filed Oct. 11, 1991, now abandoned.

BACKGROUND

This invention relates to a composition for endodontically treating a root canal, and more particularly to a composition which may be used for filling the inside of the canal after conventional endodontic treatment.

In endodontic therapy (root canal), a dentist often operates on a diseased pulp by filling in the root canal. More particularly, the dentist first accesses the root canal. The dentist then debrides the canal by removing all of the soft tissue (the pulp) contained therein. Once this is completed, the dentist typically irrigates the canal to remove pulpal remnants. Finally, the dentist then enlarges the canal to remove irregularities or rough surfaces therealong so that the dentist can insert into the canal a filling material referred to in dentistry as a "cone" or "point".

Most filling materials comprise a substance known as gutta percha which is a thermoplastic material. Gutta percha is very opaque because it includes a substantial amount of zinc oxide (approximately 70%). Gutta percha is usually applied in the shape of a cone or point of about 1.5 inches long and varying in diameter from 0.010 inches to 0.090 inches.

When using a cone made of gutta percha in a root canal treatment, it is desirable to have the point of the cone terminate at the apex in the canal. In prior methodologies, repeated x-rays of the patient's mouth were required in order to 1) place the point accurately at the apex and 2) prevent the material from going over the apex during seating and compacting. Moreover, this x-ray technique was not always accurate because the apex of the tooth is curved—when it appears on the x-ray that the gutta percha is shy of the apex, it may actually very well be at or over the apex. If the gutta percha is then forced beyond the apex, a pulpal irrigation may be created.

Because of the disadvantage of using x-rays, it has been previously disclosed to use a gutta percha cone that is impregnated with electrical conductive carbon fibers. The cone is inserted into the root canal. Then, because of the presence of the electrically conductive carbon fibers, the dentist is able to measure the proximity of the gutta percha cone to the apex of the canal. As a result, a more accurate determination of where the tooth apex is located is theoretically achieved using this system.

However, the above method of using gutta percha which is impregnated with conductive carbon fibers is less than desirable. Gutta percha is a thermoplastic material which must be heated to force the material to the apex. As the material cools a gap formation occurs at the apex and along the walls of the root. This occurs despite a cement interface between the gutta percha and the walls of the root.

In addition, the use of carbon fibers may be disadvantageous. The carbon fibers may to some extent leak out over time because they have been incorporated into a thermoplastic material. A thermoplastic material such as gutta percha is very weak and inadequately holds the conductive carbon fibers in place therein.

Furthermore, as described, because a thermoplastic material such as gutta percha is used, it is necessary to heat the gutta percha during insertion. When the gutta percha is heated, the conductive materials will tend to migrate away from the center of the gutta percha, further weakening the gutta percha's hold on the carbon fibers.

Accordingly, it would be desirable to have a composition which overcomes many of the disadvantages of using a thermoplastic polymer such as gutta percha and which can incorporate electrically conductive material so that the proximity of the inserted cone to the tooth apex in the canal may be accurately measured.

SUMMARY OF THE INVENTION

Generally speaking, in accordance With the invention, a composition for endodontically treating a root canal is provided. The composition uses a thermoset resin based material adapted for insertion into the root canal of a dental patient and an adhesive material suitable for maintaining the polymer based material in the root canal. Either one or both of the thermoset resin based material and the adhesive material is conductive. As a result, the dental practitioner is able to determine where the apex of the root canal is located by means of measuring the conductance between the thermoset resin based material and the oral mucosa and periodontal ligament. This facilitates the filling of the root canal with the polymer based material.

In one preferred embodiment, the thermoset resin based material includes a thermoset resin in an amount between about 15 and 65 weight percent, an initiator in an amount between about 2 and 40 weight percent, a plasticizer in an amount between about 0.1 and 30 weight percent and a conductive material in an amount between about 10 and 90 weight percent. The conductive material is homogeneously impregnated within the thermoset resin in order to render the material conductive.

In a second embodiment, a conductive coating is applied to the thermoset resin based material in order to render the material conductive. The conductive coating is either a thermoset resin based coating or a polyurethane based material. If the coating is a thermoset resin based coating, it includes a thermoset resin such as an epoxy resin, an initiator and a conductive material. If the conductive coating is a polyurethane based material, it includes either an aromatic or aliphatic polyurethane, a solvent, a pyrrolidone for promoting evaporation and a conductive material. With either conductive coating material, the coating is placed on the thermoset resin based material by painting, spraying or dipping.

Whether the thermoset resin based material is homogeneously impregnated with a conductive material, or is instead coated with a conductive coating, the root canal composition of the invention also includes an adhesive material. The adhesive material includes a thermoset resin based material such as an epoxy resin and an initiator to polymerize the resin. Depending upon when the dental practitioner desires to locate the apex of the root canal, a conductive material may also be added to the adhesive material.

In order to treat a patient's root canal, the thermosetting resin based material is placed into the canal so that the apex may be located. Thereafter, the adhesive material is applied in order to cement the cone to the root canal.

The root canal treatment system is advantageous since it utilizes a thermoset resin based material for insertion into the dental root canal of the patient. In the first place, a thermoset resin based material neither expands nor contracts when setting in the root canal. Thus, accurate location of the tooth apex is achieved.

In addition, incorporation of conductive material such as silver in the resin material of the cone is maintained. A thermoset resin has a much stronger matrix than a thermoplastic such as gutta percha, inhibiting leakage of the conductive material.

Accordingly, it is an object of the invention to provide an improved composition for endodontically treating a dental root canal.

Another object of the invention is to provide an improved root canal composition which enables the dentist to easily locate the tooth apex.

Yet a further object of the invention is to provide an improved root canal composition which neither expands nor contracts in size upon the application of heat.

Still another object of the invention is to provide an improved root canal composition which includes a strong polymer matrix.

A further object of the invention is to provide an improved root canal composition in which a highly electrical conductive material may be incorporated.

Yet another object of the invention is to provide an improved root canal treatment composition which reduces dental error and increases the efficiency of the dentist.

Still other objects and advantages of the invention will in part be obvious and will in part be apparent from the following description.

The invention accordingly comprises the several steps and the relation of one or more of the steps with respect to each of the others, and a composition possessing the features, properties, and relation of components which are exemplified in the following detailed disclosure. The scope of the invention will be indicated in the claims.

DETAILED DESCRIPTION OF THE PREFERRED EMBODIMENTS

The composition of the invention for endodontically treating root canal always includes a thermoset resin based material which is suitable for insertion into a patient's root canal. The thermoset resin based material includes a thermoset resin in an amount between about 10 and 65 weight percent, an initiator in an amount between about 2 and 40 weight percent and a plasticizer in an amount between about 1 and 30 weight percent.

The thermoset resin may be chosen from epoxy resins, unsaturated polyesters and phenol-formaldehyde resins. The preferred resin is an epoxy resin in an amount between about 15 and 65 weight percent. The epoxy resin is chosen from diglycidyl ether of bisphenol A, diglycidyl ether of bisphenol F, and triglycidyl p-aminophenol. The preferred epoxy resin is diglycidyl ether of bisphenol A and is present in the resin based material in an amount between about 20 and 65 weight percent.

The function of thermoset resin (i.e. epoxy resin) in the thermoset resin based material of the inventive system is to provide bulk and body for the cone composition and to incorporate a conductive material (if used in thermoset resin based material).

The thermoset resin based material also includes an initiator in an amount between about 2 and 40 weight percent. The initiator is used to polymerize the thermoset resin. The initiator is selected from amine initiators, anhydride initiators, amide initiators and organic initiators.

Amine initiators are chosen from aliphatic amines, aromatic amines and tertiary amines in an amount between about 2 and 40 weight percent.

Suitable tertiary amines include hexamethlenetetramine, 2,4,6 tris(dimethylaminoethyl) phenol, and triethanolamine. The preferred tertiary amine is hexamethylene tetramine in an amount between about 3 and 20 weight percent.

Suitable aliphatic amines are chosen from ethylene triamine, triethylene tetramine and tetraethylene pentamine. Suitable aromatic amines include methylene dianiline, metaphenylene diamine and diamino diphenylsulfone.

Besides amine initiators, other initiators include anhydrides, amides and organic acids. Anhydride initiators are chosen from succinic anhydride, itaconic hydride, phthalic anhydride, maleic anhydride and alkenyl anhydride.

Organic acid initiators which are suitable for the invention include adducts of diphenolic acid and chloroacetic acid, maleic acid, aconitic acid and oxalic acid.

Amide initiators may be chosen from diacyandiamine and acrylamides.

In addition to a thermoset resin and initiator, the thermoset based material of the inventive root canal composition includes a plasticizer in an amount between about 0.1 and 30 weight percent. The purpose of the plasticizer is to soften the chosen thermoset resin so the resin based material may be easily placed into a root canal. Suitable plasticizers include dibutoxyethoxyethyl adapate, dioctyl phthalate, dibutyl phthalate, butyl benzyl phthalate, alkyl benzyl phthalate, dialkyl adipate, 2-ethylhexyl diphenyl phosphate, isodecyl diphenyl phosphate, triphenyl phosphate as well as other esters.

The preferred plasticizer is dibutoxyethoxylethyl adapate and is present in an amount between about 0.1 and 20 weight percent.

In addition to the thermoset resin based material of the inventive root canal system including a polymer matrix material, an initiator and a plasticizer, the material may also include colorizing agents such as inorganic pigments. Inorganic pigments may include titanium dioxide and red pigments or other colored pigments in an amount between about 0.3 and 20 weight percent.

In addition, a titanium species may be added to the thermoset resin based material in order to increase the materials radiopacity. The titanium species may be added either as a powder or with a silane chemically treated surface, in an amount between about 0.3 and 15 weight percent. In particular, an epoxy based silane such as gamma-glycidoxypropyltrimethoxysilane may be added to the titanium surface to form a titanium epoxy surface material. The surface material may be added to the thermoset resin based material in an amount between about 0.3 and 10 weight percent. Other suitable silanes include gamma-methacryloxypropyltrimethoxysilane, triaminofunctional silane, amino functional silane and beta-(3,4-epoxycyclohexyl) ethyltrimethoxysilane.

In order to better describe the thermoset resin based material of the inventive composition, the following examples are provided.

| Example 1 | Weight Percent |
|---|---|
| hexamethlenetetramine | 15.0 |
| diglycidyl ether of bisphenol "A" | 70.0 |
| plasticizer (Dibuyoxyethoxyethyl adapate | 15.0 |

To prepare the thermoset resin based material (point or cone) of Example 1, 15 grams of hexamethylenetetramine are combined with 70 grams of diglycidyl ether of bisphenol A and 15 grams of dibutoxyethoxyethyl adapate and mixed thoroughly for 20 minutes until a whitish-clear solution is produced. The mixture is then heated for between about 25 and 35 minutes at 80° C. Thereafter, the mixture is allowed to cool to room temperature and is then rolled into a cone or point with the use of 3" by 3" and 12" by 12" glass slabs (the glass slabs have been previously sandblasted in order to increase surface area when rolling the mixture into a point or cone). After construction of the rolled point or cone, the point or cone is heated at 120° C. for about 40 to 55 minutes to achieve a final cure. In addition, injection molding using standard injection molding techniques can also be used.

| Example 2 | Weight Percent |
|---|---|
| hexamethlenetetramine | 20.0 |
| diglycidyl ether of bisphenol "A" | 68.0 |
| titanium powder | 2.0 |
| plasticizer (dibutyl phthalate) | 10.0 |

To prepare the thermoset resin based material (point or cone) of Example 2, the components are combined in a manner similar to that described with respect to Example 1, except that titanium powder is added to form the mixture.

| Example 3 | Weight Percent |
|---|---|
| hexamethlenetetramine | 27.0 |
| diglycidyl ether of bisphenol "A" | 62.0 |
| plasticizer (dibuyoxyethoxyethyl adapate) | 4.0 |
| titanium dioxide | 7.0 |

To prepare the thermoset resin based material (point or cone) of Example 3, the components are combined in a manner similar to that described with respect to Example 1, except that titanium dioxide is added to the mixture.

In a second preferred embodiment of the root canal system of the invention, the thermoset resin based material may also include a conductive material to render the resin based material conductive in an amount between about 10 and 90 weight percent. The conductive material is typically impregnated homogeneously into the thermoset resin based material in order to render the material conductive.

Suitable conductive materials include silver, copper, nickel and graphite. The preferred conductive material is silver in an amount between about 40 and 85 weight percent.

If the thermoset resin based material includes a conductive material, then the thermoset resin (i.e., epoxy resin) is preferably present in an amount between about 5 and 65 weight percent. The preferred resin is glycidyl ether of bisphenol A in an amount between about 5 and 45 weight percent.

In order to further describe the conductive thermoset resin based material of the inventive composition, the following examples are provided:

| Example 4 | Weight Percent |
|---|---|
| silver powder | 54.0 |
| hexamethlenetetramine | 6.0 |
| diglycidyl ether of bisphenol "A" | 30.0 |
| plasticizer (dibutoxyethoxyethyl adapate | 10.0 |

To prepare the thermoset resin based material (point or cone) of Example 4, 6 grams of hexamethylenetetramine are combined with 30 grams of diglycidyl ether of bisphenol A and 10 grams of dibutoxyethel adapate. Then, 54 grams of silver powder are added until a homogenous mixture of a dark brown color is obtained. The mixture is then heated and rolled in a manner similar to that described with respect to Example 1 in order to achieve a point or cone.

| Example 5 | Weight Percent |
|---|---|
| silver powder | 45.0 |
| hexamethlenetetramine | 10.0 |
| diglycidyl ether of bisphenol "A" | 38.0 |
| titanium powder | 2.0 |
| plasticizer (dibutyl phthalate) | 5.0 |

To prepare the thermoset resin based material (point or cone) of Example 5, the components are combined in a manner similar to that described with respect to Example 4, except that titanium powder is added to form the mixture.

| Example 6 | Weight Percent |
|---|---|
| silver powder | 45.0 |
| hexamethlenetetramine | 7.0 |
| diglycidly ether of bisphenol "A" | 31.0 |
| plasticizer (dibutoxyethoxyethyl adapate) | 4.0 |
| silanated titanium | 2.0 |
| zinc oxide | 4.0 |
| titanium dioxide | 6.0 |
| red pigment | 1.0 |

To prepare the thermoset resin based material (point or cone) of Example 6, the components are combined in a manner similar to that described with respect to Example 4, except that silanated titanium, zinc oxide, titanium dioxide and red pigment are added to form the mixture.

In each of examples 4-6, the thermoset resin based material includes a silver powder as a conductive material that has been impregnated in the resin based material.

In an alternative embodiment of the inventive root canal composition, the thermoset resin based material is treated with a conductive coating in order to render the material conductive. Suitable conductive coatings are chosen from a thermoset resin based material and a polyurethane based material.

In accordance with the invention, a thermoset resin based coating material includes a thermoset resin, in an amount between about 10 and 55 weight percent, an initiator in an amount between about 2 and 40 weight percent, and a conductive material in an amount between about 30 and 90 weight percent.

Thermoset resins that are suitable include unsaturated polyesters, phenol-formaldehyde resins and epoxy resins. The preferred resin is an epoxy resin chosen from diglycidyl ether of bisphenol A, diglycidyl ether bisphenol F and triglycidyl p-aminophenol in an amount between about 10 and 55 weight percent based on the weight of the coating. The preferred epoxy resin is diglycidyl ether of bisphenol A and is present in the thermoset resin based coating in an amount between about 10 and 45 weight percent.

The initiator component of the thermoset resin based coating is preferably chosen from amine initiators. These include tertiaryamines, aliphatic amines and aromatic amines. Specific examples of these amines are described hereinabove in connection with the amine initiators of the thermoset resin based material.

Other suitable initiators for the thermoset resin based conductive coating may be chosen from anhydride initiators, amide initiators and organic acid initiators. Suitable examples of these types of initiators are also discussed above.

In general, in connection with the thermoset resin based conductive coating, the preferred initiator is the tertiary amine hexamethlenetetramine and is present in the coating in an amount between about 2 and 20 weight percent.

The other type of conductive coating is a polyurethane based coating. The polyurethane based coating of the invention includes a polyurethane, a solvent, an evaporation promoter as well as a conductive material.

Suitable polyurethanes for the polyurethane based coating of the invention include aromatic or aliphatic polyurethanes. The polyurethane component of the coating should be present in an amount between about 10 and 55 weight percent. Aromatic polyurethanes are not water soluble, while aliphatic polyurethanes are water soluble.

Examples of aromatic (non-water based) polyurethanes are adducts of 2,4 toluene diisocyanate (2,4 TDI), 2,3 toluene diisocyanate (2,6 TDI), methyene bis (p-phenylisocyanate) (MDI) and 1,5-naphathalene diisocyanate (NDI) with either of the following polyols: polyethylene oxide (PEO), polypropylene oxide (PPO), polyiosbutylene (PIB) or polytetramethylene oxide (PTMO). Therefore, a non-water based polyurethane could be: 2,4 TDI/PPO; 2,4 TDI/PTMO; MDI/PPO; MDI/PEO; DNI/PEO or any other combination with an aromatic diisocyanate and a polyol group.

Examples of alphatic water based polyurethanes are: adducts of 1,6-hexane diisocyanate (HDI) and isophorone diisocynate (IPDI) with either of the following polyols: polyethylene oxide (PEO), poly propylene oxide (PPO), polyiosbutylene (PIB) or polytetramethylene oxide (PTMO). Therefore, a water based polyurethane could be: HDI/PPO; IPDI/PTMO or any other combination with an alphatic diisocyanate and a polyol group.

In addition, the polyurethanes could also have a chain extender group such as: ethylene glycol (EG), hexamediol (HD), 4,4 methylene bis (2-chloroaniline) (MOCA) or ethylene diamine (ED). Therefore, the polyurethanes can be: HDI/ED/PPO; IPDI/EG/PTMO (water based polyurethane) or 2,4 TDI/ED/PPO; 2,4 TDI/MOCA/PTMO; MDI/EG/PPO; MDI/ED/PEO; NDI/ED/PEO (non-water based polyurethanes).

The polyurethane based conductive coating also includes a solvent in an amount between about 10 and 50 weight percent. The preferred solvent is water. An alcohol may be used as a solvent as well, with or without the addition of water. Suitable alcohols are ethanol, methanol, isopropyl alcohol, 3-pentanol, 2-pentanol, 1-pentanol and isobutyl alcohol. The preferred alcohol is ethanol.

A ketone may be used as a solvent. Suitable ketones include methylethyl ketone, acetone, methylpropyl ketone, allylacetone, 3-hexanone and 2-hexanone. The preferred ketone is methylethyl ketone.

In order to have a rapid mechanism for drying, the polyurethane based conductive coating also includes an evaporation promoter such as a pyrrolidone based or an ether based material in an amount between about 1 and 20 weight percent. The preferred evaporation promoter is a pyrrolidone based material and this material may be chosen from N-methylpyrrolidone (NMP), 2-pyrrolidone, 2-pyrrolidoneactamine, 1-ethyl-2-pyrrolidinone and 5-methyl-2-pyrrolidinone. N-methylpyrrolidone is the preferred pyrrolidone material and is preferably present in an amount between about 1 and 15 weight percent.

If an ether is used as the evaporation promoter, the ether may be chosen from diethylether, isopropylether and pentylether.

Both the thermoset resin based coating and the polyurethane based coating also include a conductive material such as silver, copper, nickel or graphite. The conductive material in the coating would be present in an amount between about 30 and 90 weight percent. The preferred conductive material is silver and is preferably present in an amount between 60 and 85 weight percent.

In order to further describe the conductive coatings which may be used in the root canal system of the invention, the following examples are provided:

EXAMPLES OF THERMOSET RESIN BASED CONDUCTIVE COATINGS

| Example 7 | Weight Percent |
|---|---|
| silver | 70.0 |
| hexamethlenetetramine | 15.0 |
| diglycidyl ether of bisphenol "A" | 15.0 |

To prepare the thermoset resin based conductive coating of Example 7, 70 grams of silver are combined with 15 grams of hexamethylene tetramine and 15 grams of diglycidyl ether of bisphenol A. The components are mixed in order to form a dark brown putty-like mixture. The mixture is coated onto a thermoset resin based point or cone and then allowed to set at room temperature. Alternatively, the cone with the applied thermoset coating may be heated at a temperature of 80° C. for 30 to 60 minutes in order to accelerate setting of the coating.

| Example 8 | Weight Percent |
|---|---|
| silver | 75.0 |
| hexamethlenetetramine | 9.0 |
| diglycidyl ether of bisphenol "A" | 14.0 |
| titanium powder | 2.0 |

To prepare the thermoset resin based conductive coating of Example 8, the components are combined in a manner similar to that described with respect to Example 7, except that titanium powder is added to the mixture.

EXAMPLES OF POLYURETHANE BASED CONDUCTIVE COATINGS

| Example 9 | Weight Percent |
| --- | --- |
| acetone | 20.0 |
| 5-methyl-2-pyrrolidinone | 5.0 |
| silver | 60.0 |
| 2,4 TDI/ED/PPO | 15.0 |

To prepare the polyurethane based conductive coating of Example 9, 5 grams of 5-methyl-2-pyrrolidinone are mixed with 15 grams of 2,4 TDI/ED/PPO. In addition, 20 grams of acetone are mixed with 60 grams of silver in order to form an acetone slurry of silver. The acetone slurry of silver is added to the mixture of 5-methyl-2-pyrrolidinone and 2,4 TDI/ED/PPO. The resulting mixture is then coated onto a thermoset resin based cone. The polyurethane based conductive coating is then allowed to either air dry or dry by the application of a cold air source in order to accelerate evaporation.

| Example 10 | Weight Percent |
| --- | --- |
| water | 10.0 |
| N-methylpyrrolidone (NMP) | 12.0 |
| HDI/ED/PPO | 10.0 |
| silver | 68.0 |

To prepare the polyurethane based conductive coating of Example 10, the components are combined in a manner similar to that described with respect to Example 9.

With either a thermoset resin conductive coating or a polyurethane conductive coating, application to the thermoset resin based material is achieved by conventional methods such as painting, spraying or dipping. After application, the resin based material with the applied coating is allowed to dry.

The other component of the inventive root canal composition is an adhesive material, which is used in the system for maintaining the thermoset resin based material in the root canal. The adhesive material includes a thermoset resin in an amount between about 10 and 75 weight percent and an initiator in an amount between about 2 and 40 weight percent to polymerize the resin.

The thermoset resin in the adhesive material may be chosen from epoxy resins, unsaturated polyesters, and phenol-formaldehyde resins. The preferred thermoset resin is an epoxy resin present in the adhesive material in an amount between about 15 and 75 weight percent. The epoxy resin may be chosen from diglycidyl ether of bisphenol A, diglycidyl ether of bisphenol F and triglycidyl p-aminophenol. The preferred epoxy resin is diglycidyl ether of bisphenol A in amount between about 25 and 75 weight percent.

The preferred initiator for the adhesive material is an amine initiator in an amount between about 2 and 40 weight percent. The amine initiator is chosen from tertiary amines, aliphatic amines and aromatic amines—suitable amines of this type have been described in connection with the initiator component of the thermoset resin based material. The preferred amine initiator is the tertiary amine hexamethlenetetramine and is preferably present in an amount between about 2 and 20 weight percent.

Other suitable initiators for polymerizing the epoxy resin are anhydride initiators, amide initiators and organic acid initiators. Suitable ones have been described hereinabove in connection with the initiator component of the thermoset resin based material that is used in the inventive root canal composition.

Depending upon how the root canal composition of the invention is utilized, it may be desirable to add a conductive material to the adhesive material component. Suitable conductive materials are silver, copper, nickel and graphite, and are present in an amount between about 10 and 90 weight percent. The preferred conductive material is silver in an amount between about 40 and 85 weight percent.

If the adhesive material includes a conductive material, then the thermoset resin component (i.e., epoxy resin) is preferably present in the adhesive material in an amount between about 10 and 55 weight percent. The preferred resin is diglycidyl ether of bisphenol A in an amount between about 15 and 45 weight percent.

It may also be desirable to add a titanium species to the adhesive material of the inventive composition, either plain powder or chemically treated, to increase radiopacity in the adhesive material. In particular, titanium may be added either as a plain powder or with silane chemically treated surfaces in an amount between about 0.3 and 15 weight percent. For example, in accordance with the invention, it may be desirable to add an epoxy based silane such as gamma glycidoxypropyltrimethoxysilane to the titanium surface to form a titanium epoxy surface material. This material may be added to the adhesive material in an amount between about 0.3 and 10 weight percent. Other suitable silanes include gamma-methacryloxypropyltrimethoxysilane, triaminofunctional silane, aminofunctional silane and beta-(3,4-epoxycyclohexyl)-ethyltrimethoxysilane.

Furthermore, pigments may be added to the adhesive material component in an amount between about 0.3 and 20 weight percent.

In order to further describe the adhesive component of the inventive composition, the following examples are provided

NON-CONDUCTIVE ADHESIVES

| Example 11 | Weight Percent |
| --- | --- |
| hexamethlenetetramine | 10.0 |
| diglycidyl ether of bisphenol A | 50.0 |
| bismuth oxide | 15.0 |
| zinc oxide | 17.5 |
| titanium oxide | 7.5 |

To prepare the non-conductive adhesive of Example 11, a powder is first prepared by combining 10 grams of hexamethylenetetramine, 15 grams of bismuth oxide, 17.5 grams of zinc oxide and 7.5 grams of titanium dioxide. Then, 50 grams of liquid diglycidyl ether of bisphenol A is added to the powder mixture in order to form an adhesive paste.

| Example 12 | Weight Percent |
| --- | --- |
| hexamethlenetetramine | 15.0 |
| diglycidyl ether of bisphenol A | 45.0 |

-continued

| Example 12 | Weight Percent |
|---|---|
| bismuth oxide | 10.0 |
| magnesium oxide | 28.0 |
| titanium powder | 2.0 |

To prepare the non-conductive adhesive of Example 12, the components are combined in a manner similar to that described with respect to Example 11.

CONDUCTIVE ADHESIVES

| Example 13 | Weight Percent |
|---|---|
| Silver powder | 64.0 |
| hexamethlenetetramine | 6.0 |
| diglycidyl ether of bisphenol "A" | 30.0 |

To prepare the conductive adhesive of Example 13, a powder is first prepared by combining 6 grams of hexamethlenetetramine and 64 grams of silver powder. Then, 30 grams of liquid diglycidyl ether of bisphenol A is added to the powder in order to form a conductive adhesive paste.

| Example 14 | Weight Percent |
|---|---|
| Silver powder | 70.0 |
| hexamethlenetetramine | 7.0 |
| diglycidyl ether of bisphenol "A" | 10.0 |
| silanated titanium | 2.0 |
| zinc oxide | 4.0 |
| titanium dioxide | 6.0 |
| red pigment | 1.0 |

To prepare the conductive adhesive of Example 14, the components are combined in a manner similar to that described with respect to Example 13, except that silanated titanium, zinc oxide, titanium dioxide and red pigment are added to form the powder.

Application of the invention root canal composition is as follows. After a dental practitioner removes the diseased pulp from a patient's tooth, an appropriate sized thermoset resin based cone made in accordance with the invention is placed into the root canal. The thermoset resin based cone may include a conductive material substantially uniformly impregnated therein or instead be treated with a thermoset resin based conductive coating or polyurethane based conductive coating as described herein.

In order to compare the electrical conductance in the root canal to the known fixed value of the conductance between the oral mucosa and the periodontal ligament (the value is the same as at the apical foramen), an apex locator is used (a Neosono-MC manufactured by Amadent/American Medical Dental Corp. of Cherry Hill, New Jersey). An apex locator is an electronic root canal measuring device for locating the root canal apex and its use is known by those of ordinary skill in endodontic dentistry. Once the apex is located, the position and length of the thermoset resin based cone in the root canal is recorded and the cone is then ready to be cemented into the root canal using an adhesive made in accordance with the invention.

If a non-conductive adhesive of the invention is used, after placement of the conductive cone in the root canal, cone length of the root canal is recorded and the non-conductive adhesive is applied to the cone. In particular, the adhesive is first added to the canal with the use of a file or other instrument. Then the coated cone with the non-conductive adhesive is added to the root canal and placed therein such that it extends no longer than the length that was recorded when the apex of the canal was located using the apex locator. Once this is done, excess cone (that is sticking out of the coronal end of the tooth) and adhesive material is removed in a conventional manner and the root canal is sealed.

If a conductive adhesive is used instead, the conductive adhesive is first added to the root canal with the use of a file or other dental instrument. The conductive cone is then coated with the conductive adhesive and placed in the canal. With the use of an apex locator, the apex of the canal is determined and the dental practitioner withdraws the cone and cuts off the length at the apical end that went beyond the apical opening of the root. Thereafter, excess cone and adhesive material is removed in a conventional manner and the root canal is then sealed.

In an alternative embodiment, a non-conductive cone may be used with a conductive adhesive. Initially, the conductive adhesive is added to the root canal with the use of a file or other dental instrument. The non-conductive cone is then coated with the conductive adhesive and placed into the root canal. With the use of an apex locator, the root canal apex is determined and the dental practitioner will then cease penetration of the cone in the root canal. As before, excess cone and adhesive material is then removed in a conventional manner and the root canal is sealed.

To further demonstrate the effectiveness of the inventive root canal composition, the following dye study for testing in vitro apical sealability for a conductive thermoset resin based material (cone) and non-conductive adhesive material is described.,

DYE STUDY

| | Weight Percent |
|---|---|
| Conductive thermoset resin based material: | |
| silver powder | 74.0 |
| hexamethlenetetramine | 3.3 |
| diglycidyl ether of bisphenol "A" | 17.0 |
| dibutoxyethoxyethyl adapate | 5.0 |
| silanated titanium | 0.3 |
| red pigment | 0.4 |
| Non-Conductive adhesive material used: | |
| hexamethlenetetramine | 10.0 |
| diglycidyl ether of bisphenol "A" | 50.0 |
| bismuth oxide | 15.0 |
| zinc oxide | 17.5 |
| titanium dioxide | 7.5 |

A total of ten single root teeth were extracted and stored in saline solution for 24 hours. The crowns for these teeth were then removed by a diamond disk and their root canals were enlarged to a #50 K file (Kerr/Sybron, Rommulus, Mich). The enlarged canals were then funneled with a #3 Flexi-Post reamer Essential Dental Systems, Inc., S. Hackensack, N.J.). Five teeth served as the control group and five teeth were used for the test.

After enlargement of the canals for these five control teeth, the cornal portion of these teeth were then filled (approximately 3–4 mm) with an endodontic filling material (Cavit, ESPE-Premier, Norristown, Penna.). The five samples were then placed in 100% humidity for one week.

After enlargement with the #3 Flexi-Post reamer, the test teeth were then cemented with the conductive thermoset resin based material (cones) using the non-conductive adhesive material. The adhesive material was first applied to the canals with the use of a #40 K file (Kerr, Sybron, Rommulus, Mich.). Then the cones were coated with adhesive and placed in the canals. The five samples were then placed in 100% humidity for one week.

After one week at 100% humidity, the samples were dried and two coats of red nail polish (Ultra-touch, Avon Products, N.Y.) were applied to each tooth (the first coat was allowed to dry for at least six hours before the second coat was applied) except for the apical one millimeter. After the second coat was applied, the teeth were allowed to dry overnight. Dental floss was then tied around each tooth (at both the apical and cornal portions). A hook was then attached to each end of the dental floss. These teeth were then placed in a beaker (anchored with a hook) for one week in a 1% methylene blue solution (Aldrich Chemical Company, Milwaukee, Wis.) (1 gram of methylene blue/99 grams of water). Only the first 1 or 2 mm of the apical portion of the teeth were exposed to the methylene blue solution.

After one week, the teeth were placed in running water for one hour and dried. Each tooth was then sectioned and the amount of dye penetration in each canal was observed with the use of a microscope (setting at 10% power).

The results showed that the control teeth each had the blue dye penetrate approximately 90–95% of the canal length (for example, a total of 13 mm out of 14 mm was penetrated with the dye). The test teeth on the other hand, showed less than 1–5% of penetration of the dye (for example, a total of 0.5 mm out of 14 mm was penetrated with the dye).

The test demonstrates that the combination of the conductive thermoset resin based material (cone) and the non-conductive adhesive material results in minimal dye penetration at the apex. In other words, the inventive combination results in excellent sealability as a root canal filling material.

It will thus be seen that the objects set forth above, among those made apparent from the preceding description, are efficiently attained and, since certain changes may be made in the carrying out the above method and in the composition set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A method for endodontically treating a root canal comprising:
   inserting a thermoset resin based material into a patient's root canal and
   maintaining said thermoset resin based material in said root canal by application of an adhesive material;
   wherein at least one of said resin based material and said adhesive material is conductive.

2. The composition of claim 1, wherein said thermoset resin based material comprises:
   a thermoset resin in an amount between about 10 and 65 weight percent;
   an initiator in an amount between about 2 and 40 weight percent; and
   a plasticizer in an amount between about 0.1 and 30 weight percent, the weight percents based on the total weight of the thermoset resin based material.

3. The method of claim 2, wherein said thermoset resin is selected from the group consisting of epoxy resins, unsaturated polyesters and phenol-formaldehyde resins.

4. The method of claim 3, wherein said thermoset resin is an epoxy resin in an amount between about 15 and 65 weight percent.

5. The method of claim 4, wherein said epoxy resin is selected from the group consisting of diglycidyl ether of bisphenol A, diglycidyl ether of bisphenol F and triglycidyl p-aminophenol.

6. The system of claim 5, wherein said epoxy resin is diglycidyl ether of bisphenol A in an amount between about 20 and 65 weight percent.

7. The method of claim 2, wherein said initiator is selected from the group consisting of amine initiators, anhydride initiators, amide initiators and organic acid initiators.

8. The method of claim 7, wherein said amine initiators are selected from the group consisting of aliphatic amines, aromatic amines and tertiary amines in an amount between about 2 and 40 weight percent.

9. The method of claim 8, wherein said tertiary amines are selected from the group consisting of 2,4,6 tris (dimethylaminomethyl)phenol, triethanolamine and hexamethlenetetramine.

10. The method of claim 9, wherein said tertiary amine is hexamethlenetetramine in an amount between about 3 and 20 weight percent.

11. The method of claim 7, wherein said anhydride initiator is selected from the group consisting of succinic anhydride, itaconic anhydride, phthalic anhydride, maleic anhydride and alkenyl anhydride.

12. The method of claim 7, wherein said amide initiator is selected from the group consisting of diacyandiamine and acrylamides.

13. The method of claim 7, wherein said organic acid initiator is selected from the group consisting of adducts of diphenolic acid and chloroacetic acid, maleic acid, aconitic acid and oxalic acid.

14. The method of claim 2, wherein said plasticizers are selected from the group consisting of dibutoxyethoxyethyl adapate, dioctyl phthalate, dibutyl phthalate, butyl benzyl phthalate, alkyl benzyl, phthalate, dialkyl adipate, 2-ethylhexyl diphenyl phosphate, isodecyl diphenyl phosphate, triphenyl phosphate as well as other esters.

15. The method of claim 14, wherein said plasticizer is dibutoxyethoxyethyl adapate in an amount between about 0.1 and 20 weight percent.

16. The method of claim 2, wherein said thermoset resin based material further includes a titanium species in an amount between about 0.3 and 15 weight percent.

17. The method of claim 16, wherein said titanium species is selected from the group consisting of titanium powder and titanium which has been chemically treated by a silane.

18. The method of claim 17, wherein the titanium species is titanium chemically treated by gamma-glycidoxypropyltrimethoxysilane in an amount between about 0.3 and 10 weight percent.

19. The method of claim 2, wherein said thermoset resin based material further includes a conductive material for rendering the resin based material conductive in an amount between about 10 and 90 weight percent.

20. The system of claim 19, wherein said thermoset resin is an epoxy resin in an amount between about 5 and 65 weight percent.

21. The method of claim 19, wherein said conductive material is selected from the group consisting of silver, copper, nickel and graphite.

22. The method of claim 21, wherein said conductive material is silver in an amount between about 40 and 85 weight percent.

23. The method of claim 1, further including a conductive coating for application to said thermoset resin based material for rendering said thermoset resin base material conductive.

24. The method of claim 23, wherein said conductive coating is selected from a thermoset resin based coating and a polyurethane based coating.

25. The method of claim 24, wherein said thermoset resin based coating comprises:
a thermoset resin in an amount between about 10 and 55 weight percent;
an initiator in an amount between about 2 and 40 weight percent; and
a conductive material in an amount between about 30 and 90 weight percent, the weight percents based on the total weight of the thermoset resin based coating.

26. The method of claim 25, wherein said thermoset resin is selected from the group consisting of epoxy resins, unsaturated polyesters and phenol-formaldehyde resins.

27. The, composition of claim 26, wherein said thermoset resin is an epoxy resin in an amount between about 10 and 55 weight percent.

28. The method of claim 27, wherein the epoxy resin is diglycyl ether of bisphenol A in an amount between about 10 and 45 weight percent.

29. The method of claim 28, wherein the initiator is selected from the group consisting of amine initiators, anhydride initiators, amine initiators and organic initiators.

30. The method of claim 29, wherein the amine initiators are selected from the group consisting of aliphatic amines, aromatic amines and tertiary amines.

31. The method of claim 30, wherein the tertiary amine is hexamethylene tetramine in an amount between about 2 and 20 weight percent.

32. The method of claim 25, wherein conductive material is selected from the group consisting of silver, copper, nickel and graphite.

33. The method of claim 32, wherein the conductive material is silver in an amount between about 60 and 85 weight percent.

34. The method system of claim 24, wherein the polyurethane based coating comprises:
a polyurethane in an amount between about 10 and 55 weight percent;
a solvent in an amount between about 10 and 50 weight percent;
an evaporation promoter in an amount between about 1 and 20 weight percent; and
a conductive material in an amount between about 30 and 90 weight percent, the weight percents based on the total weight of the polyurethane based coating.

35. The method of claim 34, wherein the polyurethane is selected from the group consisting of aromatic and aliphatic polyurethanes.

36. The method of claim 34, wherein the solvent is selected from the group consisting of water, alcohols and ketones.

37. The method of claim 36, wherein the alcohols are selected from the group consisting of ethanol, methanol, isopropyl alcohol, 3-pentanol, 2-pentanol, 1-pentanol and isobutyl alcohol.

38. The method of claim 36, wherein the ketones are selected from the group consisting of methylethyl ketone, acetone, methylpropyl ketone, allyl acetate, 3-hexanone and 2-hexanone.

39. The method of claim 34, wherein the evaporation promoter is selected from the group consisting of a pyrrolidone based material and an ether based material.

40. The method of claim 39, wherein the evaporation promoter is a pyrrolidone based material selected from the group consisting of N-methylpyrrolidone, 2-pyrrolidone, 2-pyrrolidoneactamine, 1-ethyl-2-pyrrolidinone and 5-methyl-2-pyrrolidinone.

41. The method of claim 40, wherein the pyrrolidone based material is N-methylpyrrolidone in an amount between about 1 and 15 weight percent.

42. The method of claim 34, wherein the conductive material is selected from the group consisting of silver, copper, nickel and graphite.

43. The method of claim 42, wherein the conductive material is silver in an amount between about 60 and 85 weight percent.

44. The method of claim 1, wherein said adhesive material comprises:
a thermoset resin in an amount between about 10 and 75 weight percent and an initiator in an amount between about 2 and 40 weight percent, the weight percents based on the total weight of the adhesive material.

45. The method of claim 44, wherein said thermoset resin is selected from the group consisting of epoxy resins, unsaturated polyesters and phenol-formaldehyde resins.

46. The method of claim 45, wherein said epoxy resin is selected from the group consisting of diglycidyl ether of bisphenol A, diglycidyl ether of bisphenol F and triglycidyl p-aminophenol.

47. The method of claim 46, wherein said epoxy resin is diglycidyl ether of bisphenol A in an amount between about 25 and 75 weight percent.

48. The method of claim 44, wherein said initiator is selected from the group consisting of amine initiators, anhydride initiators, amine initiators and organic acid initiators.

49. The method of claim 48, wherein said amine initiators are selected from the group consisting of tertiary amines, aliphatic amines and aromatic amines.

50. The method of claim 49, wherein the tertiary amine is hexamethylenetetramine in an amount between about 3 and 20 weight percent.

51. The method of claim 44, wherein the adhesive material further includes a titanium species in an amount between about 0.3 and 15 weight percent.

52. The method of claim 51, wherein said titanium species is selected from the group consisting of titanium powder and titanium which has been chemically treated by a silane.

53. The method of claim 52, wherein the titanium species is titanium chemically treated by gamma-glycidoxypropyltrimethoxy silane in an amount between about 0.3 and 10 weight percent.

54. The method of claim 44, further including a conductive material in an amount between about 10 and 90 weight percent.

55. The method of claim 54, wherein the thermoset resin is an epoxy resin in an amount between about 10 and 55 weight percent.

56. The method of claim 54, wherein said conductive material is selected from the group consisting of silver, copper, nickel and graphite.

57. The method of claim 56, wherein said conductive material is silver in an amount between about 40 and 85 weight percent.

58. A method for endodontically treating a root canal comprising:
- inserting a thermoset resin based material into a patient's root canal, said thermoset resin based material comprising a thermoset resin in an amount between about 15 and 65 weight percent, an initiator in an amount between about 2 and 40 weight percent, a plasticizer in an amount between about 0.1 and 30 weight percent and a conductive material in an amount between about 10 and 90 weight percent; and
- maintaining said thermoset resin based material in said root canal by application of an adhesive material comprising a thermoset resin in an amount between about 10 and 75 weight percent and an initiator in an amount between about 2 and 40 weight percent.

59. The method of claim 58, wherein both of said thermoset resins are epoxy resins and both of said initiators are tertiary amines.

60. The method of claim 59, wherein said thermoset resin based material comprises diglycidyl ether of bisphenol A in an amount between about 20 and 45 weight percent, hexamethylene tetramine in an amount between about 3 and 20 weight percent, dibutoxyethoxyethyl adapate in an amount between about 0.1 and 20 weight percent and silver in an amount between about 40 and 85 weight percent; and
- wherein said adhesive material includes diglycidyl ether of bisphenol A in an amount between about 15 and 70 weight percent and hexamethylenetetramine in an amount between about 3 and 20 weight percent.

61. The method of claim 59, wherein said thermoset resin based material further includes a titanium species in an amount between about 0.3 and 15 weight percent.

62. The method of claim 61, wherein said thermoset resin based material further includes titanium that has been chemically treated by gamma glycidoxypropyltrimethoxysilane in an amount between about 0.3 and 10 weight percent.

63. A method for endodontically treating a root canal comprising:
- applying a conductive coating to a thermoset resin based material;
- inserting said thermoset resin based material into a patient's root canal; and
- maintaining said thermoset resin based material in said root canal by application of an adhesive material.

64. The method of claim 63, wherein said thermoset resin based material comprises thermoset resin in an amount between about 10 and 65 weight percent, an initiator in an amount between about 2 and 40 weight percent and a plasticizer in an amount between about 0.1 and 30 weight percent;
- wherein said conductive coating is selected from the group consisting of a thermoset resin based coating and a polyurethane based coating; and
- wherein said adhesive material comprises a thermoset resin in an amount between about 10 and 75 weight percent and an initiator in an amount between about 2 and 40 weight percent.

65. The method of claim 64, wherein said thermoset resin based coating comprises:
- a thermoset resin in an amount between about 10 and 55 weight percent;
- an initiator in an amount between about 2 and 40 weight percent; and
- a conductive material in an amount between about 30 and 90 weight percent, the weight percents based on the total weight of the thermoset resin based coating.

66. The composition of claim 64, wherein said polyurethane based coating comprises:
- a polyurethane in an amount between about 10 and 55 weight percent;
- a solvent in an amount between about 10 and 50 weight percent;
- an evaporation promoter in an amount between about 1 and 20 weight percent; and
- a conductive material in an amount between about 30 and 90 weight percent.

* * * * *